(12) United States Patent
Portoghese et al.

(10) Patent No.: US 6,534,514 B1
(45) Date of Patent: *Mar. 18, 2003

(54) KAPPA OPIOID RECEPTOR ANTAGONISTS

(75) Inventors: Philip S. Portoghese, St. Paul, MN (US); Sandra L. Olmsted, Richfield, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/449,224

(22) Filed: May 24, 1995

Related U.S. Application Data

(63) Continuation of application No. 08/080,287, filed on Jun. 21, 1993, now Pat. No. 5,457,208.

(51) Int. Cl.$^7$ .................... A61K 31/439; C07D 491/18

(52) U.S. Cl. .......................... 514/279; 546/35

(58) Field of Search ............... 514/279; 546/35

(56) References Cited

U.S. PATENT DOCUMENTS

| | | | |
|---|---|---|---|
| 4,362,870 A | * 7/1982 | Portoghese | 546/46 |
| 4,401,672 A | * 8/1983 | Portoghese | 514/282 |
| 4,649,200 A | 3/1987 | Portoghese et al. | 546/26 |
| 4,730,848 A | * 3/1988 | Portoghese | 546/45 |
| 4,761,429 A | 8/1988 | Blum et al. | 514/561 |
| 4,806,556 A | * 2/1989 | Portoghese | 546/45 |
| 4,816,586 A | 3/1989 | Portoghese | 544/340 |
| 4,882,335 A | 11/1989 | Sinclair | 514/282 |
| 5,086,058 A | 2/1992 | Sinclair et al. | 514/282 |
| 5,223,507 A | * 6/1993 | Dappen et al. | 514/279 |
| 5,225,417 A | * 7/1993 | Dappen et al. | 514/279 |
| 5,352,680 A | * 10/1994 | Portoghese | 514/279 |
| 5,354,863 A | * 10/1994 | Dappen et al. | 546/35 |
| 5,436,249 A | * 7/1995 | Dappen | 514/279 |
| 5,457,208 A | * 10/1995 | Portoghese | 546/35 |

FOREIGN PATENT DOCUMENTS

| | | |
|---|---|---|
| WO | WO 85/00970 | 3/1985 |

OTHER PUBLICATIONS

G. T. Bain, et al., "Naloxone Attenuation of the Effect of Cocaine on Rewarding Brain Stimulation," *Life Science*, 40, pp. 1119–1135, (1987).

E. J. Bilsky, et al., "Using Antagonists to Assess Neurochemical Coding of a Drug's Ability to Establish a Conditioned Place Preference," *Pharmacol. Biochem. Behav.*, 37, pp. 425–431, (1990).

D. R. Brown, et al., "Suppression of Deprivation–Induced Food and Water Intake in Rats and Mice by Naloxone," *Pharmacol. Biochem. Behav.*, 11, pp. 567–573, (1979).

J. C. Froehlich et al., "Delta Opioid Antagonists Produce Prolonged Suppression of Ethanol Intake", *The Official Journal of The Research Society on Alcoholism and International Society for Biomedical Research on Alcoholism; Alcoholism Clinical and Experimental Research*, 15, Abstract 20, (Apr. 1991).

J.C. Froehlich et al., "Importance of Delta Opioid Receptors in Maintaining High Alcohol Drinking", *Psychopharmacology*, 103, pp. 467–472, (1991).

J.C. Froehlich et al., "Naloxone Attenuates Voluntary Ethanol Intake in Rats Selectively Bred for High Ethanol Preference", *Pharmacology Biochemistry & Behavior*, 35, pp. 385–390, (1990).

M. Gates et al., "Some Potent Morphine Antagonists Possessing High Analgesic Activity", *Potent Morphine Antagonists*, 7, pp. 127–131, (Mar. 1964).

J. J. Gromley, et al., "In Vivo Evaluation of the Opiate Delta Receptor Antagonist ICI 154,129," *Life Sciences*, 31, pp. 1263–1266, (1982).

G. Henderson et al., "A New Example of a Morphine–Sensitive Neuro–Effector Junction: Adrenergic Transmission in the Mouse Vas Deferens", *Brit. J. Pharmacol.*, 46, pp. 764–766 (1972).

S. G. Holtzman, et al., "Effects of Narcotic Antagonists on Fluid Intake on the Rat," *Life Sciences*, 16, pp. 1465–1470, (1975).

S. G. Holtzman, et al., "Suppression of Appetitive Behavior in the Rat by Naloxone: Lack of Effect of Prior Morphine Dependence," *Life Sciences*, 24, pp. 219–226, (1979).

(List continued on next page.)

Primary Examiner—Richard L. Raymond
(74) Attorney, Agent, or Firm—Schwegman, Lundberg, Woessner & Kluth, P.A.

(57) ABSTRACT

Compounds of the formula:

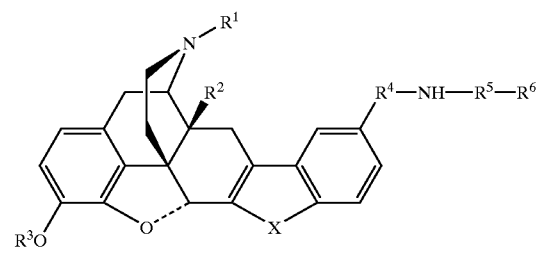

are provided, which are selective kappa opioid receptor antagonists, wherein $R^1$ is $(C_1-C_5)$alkyl, $C_3-C_6$(cycloalkyl)alkyl, $C_5-C_7$(cycloalkenyl)alkyl, $(C_6-C_{12})$aryl, $(C_6-C_{12})$aralkyl, trans$(C_4-C_5)$alkenyl, allyl or furan-2-ylalkyl, $R^2$ is H, OH or $O_2C(C_1-C_5)$alkyl; $R^3$ is H, $(C_6-C_{10})$aralkyl, $(C_1-C_5)$alkyl or $(C_1-C_5)$alkylCO; X is O, S or NY, wherein Y is H or $(C_1-C_5)$ alkyl; $R^4$ is $CH_2$ (methylene) or C=O (carbonyl), $R^5$ is $CH_2$, C=O or C=NH (imino) and $R^6$ is $(C_1-C_4)$alkyl or NH$(C_1-C_4)$alkyl, optionally substituted by a non-terminal $(C_1-C_2)$alkyl group or by N$(R^7)(R^8)$ wherein $R^7$ and $R^8$ are individually H or $(C_1-C_3)$alkyl, with the proviso that one of $R^4$ or $R^5$ is $CH_2$, and the pharmaceutically acceptable salts thereof.

10 Claims, No Drawings

OTHER PUBLICATIONS

P.S. Portoghese, "Design of Peptidomimetic δ Opioid Receptor Antagonists Using the Message–Address Concept", *Journal of Medicinal Chemistry*, 33, pp. 1714–1720, (1990).

P.S. Portoghese et al., "Only One Pharmacophore is Required for the k Opioid Antagonist Selectively of Norbinaltorphimine", *Journal of Medicinal Chemistry*, 31, pp. 1344–1347, (1988).

J. S. Shaw, et al., "Selective Antagonists at the Opiate Delta–Receptor", *Life Sciences*, 31, pp. 1259–1262, (1982).

M. Sofuoglu et al., "Differential Antagonism of Delta Opioid Agonists by Naltrindole and its Benzofuran Analog (NTB) in Mice: Evidence for Delta Opioid Receptor Subtypes", *The Journal of Pharmacology and Experimental Therapeutics*, 257, pp. 676–680, (1981).

J.R. Volpicelli et al., "Naltrexone and the Treatment of Alcohol–Dependence: Initial Observations", In:*Opioids, Bulimia, and Alcohol Abuse & Alcoholism*, Reid, L. D., (ed.), Springer–Verlag, New York, pp. 195–214 (1990).

S.J. Ward et al., "Improved Assays for the Assessment of k–and δ–Properties of Opioid Ligands", *European Journal of Pharmacology*, 85, pp. 163–170, (1982).

L.L. Werling et al., "Opioid Binding to Rat and Guinea–Pig Neural Membranes in the Presence of Physiological Cations at 37°C", *The Journal of Pharmacology and Experimental Therapeutics*, 233, pp. 722–728, (1985).

H. C. Jackson et al., "Are δ–Opioid Receptors Involved in the Regulation of Food and Water Intake?" *Neuropharmacol.*, 24, pp. 885–888, (1985).

R. P. Maickel, et al., "The Effects of Various Narcotic Agonists and Antagonists on Deprivation–Induced Fluid Consumption," *Neuorpharmacol.*, 16, pp. 863–866, (1977).

W.R. Martin, "Pharmacology of Opioids", *Pharmacological Reviews*, 35, pp. 283–323, (1984).

M. J. Millan, et al., "Long–Term Blockade of μ–Opioid Receptors Suggests a Role in Control of Ingestive Behavior, Body Weight and Core Temperature in the Rat," *Brain Res.*, 450, pp. 247–258, (1988).

S.L. Olmsted et al., "A Remarkable Change of Opioid Receptor Selectively on the Attachment of a Peptiodomimetic k Address Element to the δ Antagonist, Natrindole: 5'-[(N$^2$–Alkylamidino)methyl]naltrindole Derivatives as a Novel Class of k Opioid Receptor Antagonists" *Journal of Medicinal Chemistry*, 36, pp. 179–180, (1993).

P. S. Portoghese et al., "Application of the Message–Address Concept in the Design of Highly Potent and Selective Non–Peptide δ Opioid Receptor Antagonists", *Journal of Medicinal Chemistry*, 31, pp. 281–282, (Feb. 1988).

P.S. Portoghese, "Bivalent Ligands and the Message–Address Concept in the Design of Selective Opioid Receptor Antagonists", *Trends Pharmacol. Sci.*, 10, pp. 230–235, (Jun. 1989).

* cited by examiner

KAPPA OPIOID RECEPTOR ANTAGONISTS

This is a continuation of application Ser. No. 08/080,287, filed Jun. 21, 1993, now U.S. Pat. No. 5,457,208.

This invention was made with the assistance of the Government under a grant from the National Institutes of Health (Grant No. DA 01533). The U.S. Government has certain rights in the invention.

BACKGROUND OF THE INVENTION

Endogenous opioid peptides are involved in the mediation or modulation of a variety of mammalian physiological processes, many of which are mimicked by opiates or other non-endogenous opioid ligands. Some of the effects that have been investigated are analgesia, tolerance and dependence, appetite, renal function, gastrointestinal motility, gastric secretion, learning and memory, mental illness, epileptic seizures and other neurological disorders, cardiovascular responses, and respiratory depression.

The fact that the effects of endogenous and exogenous opioids are mediated by at least three different types [mu ($\mu$), delta ($\delta$), kappa ($\kappa$)] of opioid receptors raises the possibility that highly selective exogenous opioid agonist or antagonist ligands might have therapeutic applications. See W. R. Martin, *Pharmacol. Rev.*, 35, 283 (1983). Thus, if a ligand acts at a single opioid receptor type or subtype, the potential side effects mediated through other opioid receptor types can be minimized or eliminated.

The prototypical opioid antagonists, naloxone and naltrexone, are used primarily as pharmacologic research tools and for the reversal of toxic effects of opioids in case of overdose. Since these antagonists act at multiple opioid receptors, their applications in other therapeutic areas or as pharmacologic tools appear to be limited. However, naltrexone recently was reported to reduce the incidence of relapse in recovering alcoholics by J. R. Volpicelli et al., *Opioids, Bulimia and Alcohol Abuse and Alcoholism*, L. D. Reid, ed., Springer-Verlag (1990) at pages 195–214. Naloxone has been reported to suppress ethanol but not water intake in a rat model of alcoholism. J. C. Froehlich et al., *Pharm. Biochem. Behav.*, 35, 385 (1990).

Some progress has been made in the development of highly selective opioid antagonists. For example, Portoghese et al. (U.S. Pat. No. 4,816,586) disclose certain opiate analogs which possess high selectivity and potency at delta receptors. Minimal involvement was observed at mu and kappa opioid receptors. One of the highly selective analogs disclosed in U.S. Pat. No. 4,816,586 has been named "naltrindole" or "NTI," and has the formula:

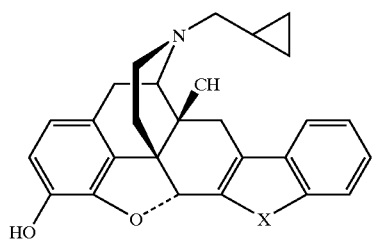

(NTI)

wherein X is NH. See P. S. Portoghese et al., *J. Med. Chem.*, 31, 281 (1988).

Portoghese et al. (U.S. Pat. No. 4,649,200) disclose substituted pyrroles which exhibit selective antagonism at kappa opioid receptors. One such analog is norbinaltrophimine (norBNI), which has the formula:

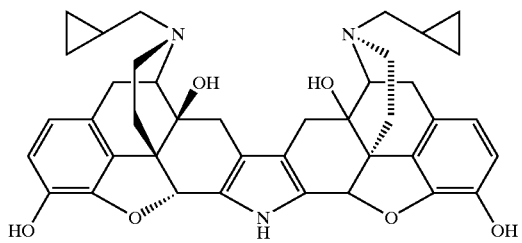

The selectivities of these prototypical $\delta$ and $\kappa$ opioid receptor antagonists have been attributed to the presence of nonpeptide "address" mimics which bear a functional relationship to key elements in the putative $\delta$ and $\kappa$ addresses of enkephalin and dynorphin, respectively. See, P. S. Portoghese et al., *Trends Pharmacol. Sci.*, 10, 230 (1989). Accordingly, the design of NTI employed a model that envisaged the Phe[4] phenyl group of enkephalin as a critical part of the $\delta$ address. See, P. S. Portoghese et al., *J. Med. Chem.*, 33, 1714 (1990). Similarly, the address element conferring selectivity in norBNI has been suggested to be a basic function that mimics the guanidinium moiety of Arg[7] in dymorphin, by P. S. Portoghese et al., *J. Med. Chem.*, 31, 1344 (1988).

It has recently been reported that suppression of ethanol ingestion may be mediated by the delta opioid receptor type. For example, the $\delta$ antagonist, N,N-diallyl-Tyr-Aib-Aib-Phe-Leu-OH (ICI 174864), strongly inhibits ethanol drinking, but has a very short duration of action, which may limit its clinical utility. See J. C. Froehlich et al., *Psychopharmacol.*, 103, 467 (1991). Using NTI as an antagonist, M. Sofuoglu et al., *J. Pharmacol. Exp. Ther.*, 257, 676 (1991) determined that the antinociceptive activity of two delta receptor agonist enkephalin analogs, DSLET and DPDPE, may be mediated by two discrete delta opioid receptor subtypes. It has also been suggested that development of addiction and/or tolerance to opiates may be inhibited by delta-opioid receptor antagonists, and that opioid-type delta-opioid receptor antagonists may be useful as immunosuppressive agents. Likewise, compounds which are selective at mu receptors may be useful as analgesics which do not exhibit the potentially harmful side effects of less-selective analgesics such as morphine.

Therefore, a continuing need exists for compounds which are opioid receptor-selective, i.e., which can act as agonists or antagonists with specificity at the delta, mu or kappa opioid receptor, or at one of the subtypes of these receptors.

SUMMARY OF THE INVENTION

The present invention is directed to biologically active compounds of formula (I):

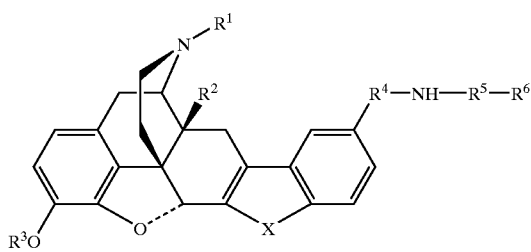

wherein $R^1$ is $(C_1-C_5)$alkyl, $C_3-C_6$(cycloalkyl)alkyl, $C_5-C_7$-(cycloalkenyl)alkyl, $(C_6-C_{12})$aryl, $(C_6-C_{12})$aralkyl, trans-$(C_4-C_5)$alkenyl, allyl or furan-2-ylalkyl, $R^2$ is H, OH or $O_2C(C_1-C_5)$alkyl; $R^3$ is H, $(C_6-C_{10})$aralkyl, $(C_1-C_5)$ alkyl or $(C_1-C_5)$alkylCO; X is O, S or NY, wherein Y is H or $(C_1-C_5)$-alkyl; $R^4$ is $CH_2$ (methylene) or C=O (carbonyl), $R^5$ is $CH_2$, C=O or C=NH (imino) and $R^6$ is $(C_1-C_4)$alkyl or $NH(C_1-C_4)$alkyl, optionally substituted by a non-terminal $(C_1-C_2)$alkyl group or by $N(R^7)(R^8)$ wherein $R^7$ and $R^8$ are individually H or $(C_1-C_3)$alkyl, with the proviso that one of $R^4$ or $R^5$ is $CH_2$, and the pharmaceutically acceptable salts thereof.

Using peptide antagonists of known binding selectivity as standards, it was unexpectedly found that the compounds of the invention are selective antagonists at kappa opioid receptors, while exhibiting little or no binding at delta or mu receptors. Thus, the present invention also provides a method for blocking kappa opioid receptors in mammalian tissue comprising contacting said receptors in vivo or in vitro with an effective amount of the compound of formula I, preferably in combination with a pharmaceutically acceptable vehicle. Thus, the compounds of formula I can be used as pharmacological and biochemical probes of opiate receptor structure and function, e.g., to measure the selectivity of other known or suspected opioid receptor antagonists or agonists. Such tissue includes tissue of the central nervous system (CNS), the gut, the cardiovascular system, the lung, the kidney, reproductive tract tissue and the like. Therefore, the compounds of formula I which exhibit kappa receptor antagonist activity may also be therapeutically useful in conditions where selective blockage of kappa receptors is desired. This includes blockage of the appetite response, blockage of paralysis due to spinal trauma and a variety of other physiological activities that may be mediated through kappa receptors.

The alkyl moiety present in the $R^1$ group which links the cycloalkyl, cycloalkenyl, aryl, or furan-2-yl moiety to the basic nitrogen atom in the compounds of formula I is a lower(alkyl) group, preferably —$(CH_2)_n$—, wherein n is about 1–5, most preferably n is 1, e.g., $R^1$ is $C_3-C_6$ (cycloalkyl)methyl, $C_5-C_7$(cycloalkenyl)-methyl, arylmethyl or furan-2-yl-methyl. Preferred aryl moieties include $(C_6-C_{10})$aryl, i.e., phenyl, benzyl, tolyl, napthyl, xylyl, anisyl and the like.

In structure I, a bond designated by a wedged or darkened line indicates one extending above the plane of the $R^3O$-substituted phenyl ring. A bond designated by a broken line indicates one extending below the plane of the phenyl ring.

Preferred compounds of the formula I are those wherein $R^1$ is $(C_1-C_5)$alkyl, $C_3-C_6$(cycloalkyl)alkyl or $C_5-C_7$-(cycloalkenyl)alkyl, preferably wherein $R^1$ is $C_3-C_6$ (cycloalkyl)methyl, and most preferably wherein $R^1$ is cyclopropylmethyl. $R^2$ is preferably OH or OAc ($O_2CCH_3$), and $R^3$ preferably is H. Preferably, X is NH or $NCH_3$, most preferably NH. Preferably, $R^6$ is methyl, ethyl, propyl, butyl or 2-methylbutyl which is unsubstituted or is terminally substituted with $N(CH_3)_2$ or $N(CH_2CH_3)_2$. Preferably, $R^4$ is $CH_2$ and $R^5$ is C=O or C=NH.

Since the compounds of the invention are formally morphinan derivatives, it is believed that their ability to cross the "blood-brain barrier" and to affect the central nervous system (CNS) should be far superior to peptide opioid antagonists. For example, as disclosed in U.S. patent application Ser. No. 07/750,109, filed Aug. 26, 1991, both NTI and its benzofuran analog, NTB were found to produce unexpectedly prolonged suppression of ethanol drinking in rats that were selectively bred for high voluntary ethanol drinking, as compared to peptidyl delta-opioid receptor antagonists. Processes of preparing the compounds of formula I are also aspects of the invention, as described hereinbelow, as are the novel intermediates employed in the syntheses.

DETAILED DESCRIPTION OF THE INVENTION

The compounds of formula I wherein X is NH can be readily synthesized by reaction of a 4,5-epoxy-6-ketomorphinan such as naltrexone (6) with 4-hydrazinobenzonitrile (D. E. Rivett et al., *Austr. J. Chem.*, 32 1601 (1979)) under Fischer indole conditions, as shown in Scheme I, to yield the 5'-nitrile 7.

Scheme I

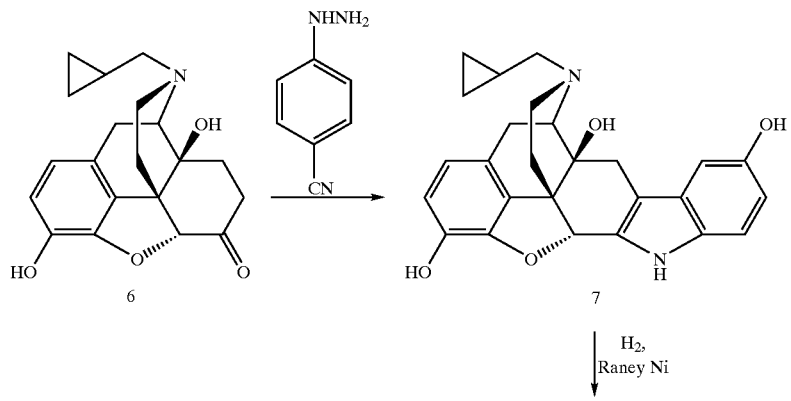

-continued

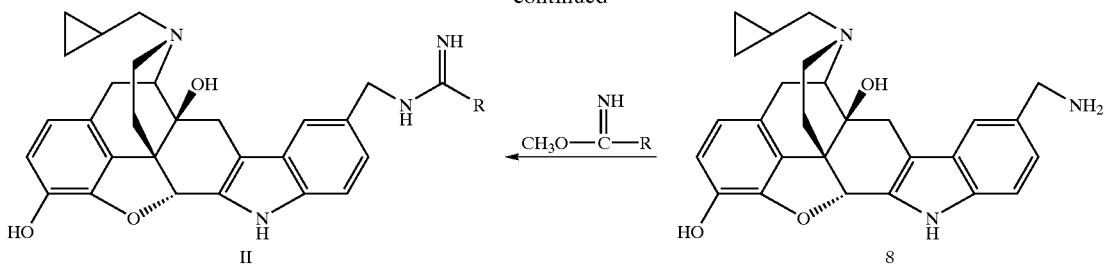

Nitrile 7 was reduced to primary amine 8 using Raney Ni, and 8 was reacted with the appropriate imidate esters, of the formula CH₃OC(=NH)—R, to yield amidates of general formula II, wherein R is ethyl, 2-methylbutyl, methyl, pentyl, propyl and butyl, respectively, for compounds 1–6.

See, S. R. Sandler et al., *Organic Chemistry*, Vol. 3, Academic Press, NY (1972) at pages 268–299; and E. Cereda et al., *J. Med. Chem.*, 33, 2108 (1990).

Compounds of formula I wherein $R^4$ is C=O can be prepared by reacting a morphinan such as naltrexone with 4-carboxyphenylhydrazine to yield a compound of formula 7 wherein the 5'-CN group has been replaced by a 5'-carboxy group, i.e., compound 15, hereinbelow. The 5'-carboxy intermediate is then amidated, e.g., with an alkylamine of the formula $H_2NR^5R^6$, wherein $R^5$ is $CH_2$ and $R^6$ is as defined above, to yield the final products.

Compounds of formula I wherein $R^4$ is $CH_2$ and $R^5$ is C=O can be prepared by reacting the 5'-$CH_2NH_2$ group, i.e., of compound 8 with a carboxylic acid of the general formula $HO_2CR^6$ wherein $R^6$ is as defined above, in the presence of benzotriazol-1-yloxy-tris(dimethylamino) phosphonium hexafluorophosphate ("BOP Reagent," Aldrich Chem. Co.).

Compounds of formula I wherein $R^4$ is $CH_2$, $R^5$ is C=NH and $R^6$ is NH($C_1$–$C_4$)alkyl, optionally substituted by non-terminal (C–$C_2$)alkyl or by N($R^7$)($R^8$) can be prepared by reacting, i.e., a compound of formula 8 with a compound of the formula $R^6$—C(OMe)=NH, wherein $R^6$ is as defined immediately above.

Compounds of formula I wherein X is O, S or NY can be prepared from intermediates analogous to 7 or 8 wherein NH has been replaced by O, S or NY. These intermediates can be prepared as generally disclosed in U.S. Pat. No. 4,816,586, which is incorporated by reference herein, which also discloses methods suitable for the preparation of salts of compounds of formula I.

The structures, common names and Merck Index reference numbers of representative 4,5-epoxy-6-ketomorphinan starting materials of general formula (III) are summarized on Table I, below.

TABLE I

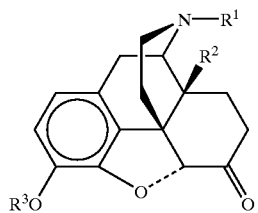

(III)

| $R^1$ | $R^2$ | $R^3$ | Common Name | Merck No.[2] |
|---|---|---|---|---|
| $CH_2CH(CH_2)_2$ | OH | H | naltrexone | 6209 |
| $CH_3$ | OH | H | oxymorphone | 6837 |
| $CH_3$ | H | H | hydromorphone | 4714 |
| $CH_3$ | H | $CH_3$ | hydrocodone | 4687 |
| $CH_2CH(CH_2)_2$ | H | H | — | —[1] |
| $CH_2CH=CH_2$ | OH | H | naloxone | 6208 |
| $CH_3$ | OH | $CH_3$ | oxycodone | 6827 |

[1]Preparation: M. Gates et al., J. Med. Chem., 7, 127 (1964).
[2]The Merck Index, W. Windholz, ed., Merck & Co., Rahway, NJ (10th ed. 1983).

Other starting materials of the general formula III can be prepared by synthetic methods which are well known in the art of organic chemistry. For example, compounds wherein $R^1$ is H and $R^3$ is a suitable protecting group, and wherein the 6-keto group has also been protected, can be prepared from the compounds of formula III. These intermediates can be N-alkylated and deprotected to yield compounds of formula I wherein $R^1$ is $C_2$–$C_5$(alkyl), $C_4$–$C_6$(cycloalkyl) alkyl, $C_5$–$C_7$(cycloalkenyl)alkyl, aryl, aralkyl, trans-$C_4$–$C_5$alkenyl or furan-2-ylalkyl, by the application of well-known reactions.

For example, the free hydroxyl groups of the compounds of formula III, e.g., $R^2$=OH and/or $R^3$=H, can be protected by acid-labile groups such as tetrahydropyranlyl, trimethylsilyl, 1-methoxy-isopropyl and the like as disclosed in *Compendium of Organic Synthetic Methods*, I. T. Harrison et al., eds., Wiley-Interscience, New York, N.Y. (1971) at pages 124–131, (hereinafter "Compendium"). The protection of the 6-keto group of compounds of Table I by its reversible conversion into a ketal or a thioketal group is disclosed in *Compendium*, at pages 449–453. Methods for the demethylation of N-methyl amines have been disclosed, for example, in *Compendium* at page 247, *J. Amer. Chem. Soc.*, 89, 1942 (1967) and *J. Amer. Chem. Soc.*, 77, 4079 (1955).

Procedures for the alkylation of secondary amines with halides under basic or neutral conditions are well known. For example, see *Compendium* at pages 242–245; *Orq. Synth.*, 43, 45 (1963); *J. Org. Chem.*, 27, 3639 (1962) and *J. Amer. Chem. Soc.*, 82, 6163 (1960).

Compounds of formula III wherein $R^2$ is acyloxy and/or $R^3$ is acyl can be prepared by using the corresponding starting materials on Table I. For example, naltrexone can be diacylated by reacting it with the appropriate ($C_1$–$C_5$)alkyl anhydride for 10–18 hrs at 18–25° C. The resultant 3,14-diacylated compound can be converted to the 14-acylated compound by limited hydrolysis. The 3-acylated starting materials can be prepared by the short-term reaction of the compounds of Table I with the anhydride, e.g., for about 2–4 hours. The 3-acylated product can be separated from the 3,14-diacylated product by chromatography.

The acid salts of compounds of formula I wherein $R^3$=H, can be converted into the corresponding ($C_1$–$C_5$)alkoxy derivatives [$R^3$=($C_1$–$C_5$)alkyl] by dissolving the starting material in DMF and adding an excess of the appropriate ($C_1$–$C_5$)alkyl iodide and an amine such as diisopropylethylamine. The reaction can be conducted at an elevated temperature for about 4–10 hours. The final product can be purified by column chromatography.

The invention also comprises the pharmaceutically acceptable salts of the biologically active compounds of formula I together with a pharmaceutically acceptable carrier for administration in effective, non-toxic dose form. Pharmaceutically acceptable amine salts may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. These physiologically acceptable salts are prepared by methods known in the art, e.g., by dissolving the free amine bases with an excess of the acid in aqueous alcohol.

In the clinical practice of the present method, the compounds of the present invention will normally be administered orally or parenterally, as by injection or infusion, in the form of a pharmaceutical unit dosage form comprising the active ingredient in combination with a pharmaceutically acceptable carrier, which may be a solid, semi-solid or liquid diluent or an ingestible capsule or tablet. The compound or its salt may also be used without carrier material. As examples of pharmaceutical carriers may be mentioned tablets, intravenous solutions, suspensions, controlled-release devices, microcapsules, liposomes and the like. Usually, the active substance will comprise between about 0.05 and 99%, or between 0.1 and 95% by weight of the resulting pharmaceutical unit dosage form, for example, between about 0.5 and 20% of preparation intended for injection or infusion and between 0.1 and 50% of preparation, such as tablets or capsules, intended for oral administration.

The invention will be further described by reference to the following detailed examples, wherein melting points were taken using a Thomas-Hoover Melting Point apparatus in open capillary tubes, and are uncorrected. NMR data was collected at ambient temperature on a Bruker AC-200 or a GE Omega 300, using DMSO-$d_6$, and TMS as the internal reference. IR data in each case was obtained from a KBr disk on a Nicollet FT-IR instrument. Low resolution FAB mass data was obtained on a Finnigan 4000 instrument. Ion spray mass spectral data was obtained from the Biochemistry Dept. Chemicals were supplied through Aldrich, except where noted. Naltrexone hydrochloride was obtained from Mallinkrodt, BOP reagent was obtained from Peptides International. TLC Rf values were obtained on silica gel using the following solvent systems: (A) 33% EtOAc, 33% CHCl$_3$, 33% MeOH, 1% NH$_3$; (B) 95% CHCl$_3$, 5% MeOH, 0.1% NH$_3$; (C) 45% EtOAc, 45% MeOH, 5% NH$_3$. Analytical data was supplied through M-H-W Laboratories, Phoenix, Ariz.

Physiological data for guinea pig ileal longitudinal muscle (GPI) was obtained by the methodology of H. P. Rang, "Stimulant Actions of Volatile Anaesthetics on Smooth Muscle," *Brit. J. Pharmacol.*, 22, 356 (1964) on Dunkin-Hartley males; mouse vas deferens (MVD) data was obtained using Henderson's method on Swiss-Webster males (G. Henderson et al., "A New Example of a Morphine-Sensitive Neuroeffector Junction: Adrenergic Transmission in the Mouse vas Deferens," *Brit. J. Pharmacol.*, 46, 764 (1972). Guinea pig brain membrane binding assays were done on Dunkin-Hartley males using a modification of the method of L. L. Werling et al., "Opioid Binding to Rat and Guinea Pig Neural Membranes in the Presence of Physiological Cations at 37° C.," *J. Pharmacol. Exp. Ther.*, 233 722 (1985). In vivo assays were done s.c. on mice.

EXAMPLE 1

17-(Cyclopropylmethyl)-6,7-dehydro-4,5α-epoxy-3, 14-dihydroxy-5'-carboxy-6,7-2',3'-indolomorphinan Hydrochloride (15).

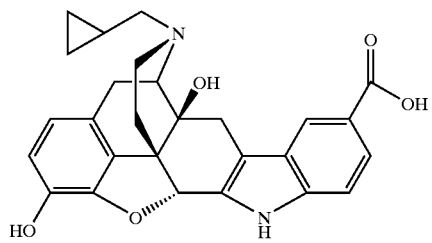

(15)

A mixture of naltrexone hydrochloride (2.0 g, 5.3 mmol) and 4-carboxyphenylhydrazine (0.934 g, 6.14 mmol) in 80 mL glacial acetic acid was stirred at 85° C. under N$_2$ 24–72 hr. Solid product was removed from the cooled crude mixture by filtration, washed with glacial acetic acid, acetone, and then ether. The solid was dissolved in methanol and dried over sodium sulfate, filtered, and the solvent removed by rotary evaporation, yielding 15 (1.8 g, 3.6 mmol, 68%). TLC(A) Rf 0.15. MS FAB (M+1) 459. IR COOH carbonyl, 1679 cm$^{-1}$.

EXAMPLE 2

17-(Cyclopropylmethyl)-6,7-dehydro-4,5α-epoxy-3, 14-dihydroxy-5'-cyano-6,7-2',3'-indolomorphinan Hydrochloride Naltrexone hydrochloride (1.0 g, 2.65 mmol) and 4-hydrazinobenzonitrile hydrochloride (3.0 mmol) were mixed in a minimum amount of glacial acetic acid and 3 drops conc. HCl and stirred at 85° C. under nitrogen for 72 hr. The cooled solution was poured into 150 mL ethyl acetate, and the solid was filtered, washed with EtOAc, then ether, and air dried. Typical yields of 7 were 50–90%. TLC (A) Rf=0.74; (B) Rf=0.30. FTIR: nitrile at 2218 cm$^{-1}$. MS FAB (M+1) 440.

EXAMPLE 3

17-(Cyclopropylmethyl)-6,7-dehydro-4,5α-epoxy-3, 14-dihydroxy-5'-aminomethyl-6,7-2',3'-indolomorphinan (8)

Nitrile 7 was reduced with H$_2$ (55 psi) in abs. methanol containing 10% NH$_3$ over Raney Ni for 4–7 days. After filtering, the solvent was removed on a rotary evaporator, and the product redissolved in EtOAc and washed 4× with alkaline brine. The combined organic phases were dried on $Na_2SO_4$ and $MgSO_4$, filtered, and the solvent was evaporated. Further purification was done via silica gel centrifugal chromatography (Chromatatron) using solvent system (A), when needed. Product 8 was used as the free base, with yields typically of 40–80%. TLC (A) Rf=0.25; (B) Rf=0.0; (C) Rf=0.62. MS FAB (M+1) 444. CHN: $C_{27}H_{31}N_3O_3Cl_2$.—$H_2O$.

EXAMPLE 4

17-(Cyclopropylmethyl)-6,7-dehydro-4,5α-epoxy-3, 14-dihydroxy-5'-[($N^2$-acetamidino)methyl]-6,7-2',3'-indolomorphinan Dihydrochloride (3; II R=$CH_3$))

Amine 8 (as the free base, 127 mg, 0.286 mmol) and ethylacetimidate hydrochloride (39 mg, 0.315 mmol) were dissolved in abs. ethanol plus 3 drops TEA and the mixture stirred 24 hr at 25° C. Solvents were evaporated, and the product was dissolved in EtOAc, and precipitated as the dihydrochloride salt, then recrystallized from hot EtOH/EtOAc to yield 133 mg of 3 (0.239 mmol, 83%); TLC (C) Rf=0.15. MS FAB (M+1) 485. CHN: $C_{29}H_{34}N_4O_3Cl_2.NaCl.2H_2O$ $^1$H NMR: 10.06 (bs, 1H, exch); 9.351 (bs, 3H, exch); 9.05 (bs, 1H, exch); 8.911 (s, 1H, exch); 7.405 (s, 1H); 7.387, 7.347 (d, 1H, J=8); 7.162, 7.124 (d, 1H, J=8); 6.718, 6.678 (d, 1H, J=8); 6.600, 6.561 (d, 1H, J=8); 6.56 (s, 1H, exch); 5.705 (s, 1H, $C_5\beta$); 4.506 (bs, 2H); 4.209 (bs, 1H); 3.52, 3.408, 3.32 (m, 3H); 3.11 (m, 2H); 3.03 (s, 2H); 2.68 (s, 1H); 2.66 (s, 1H) 2.137 (s, 3H); 1.768 (d, 1H); 1.155 (m, 1H); 0.690 (m, 2H); 0.497 (m, 2H).

EXAMPLE 5

17-(Cyclopropylmethyl)-6,7-dehydro-4,5α-epoxy-3, 14-dihydroxy-5'-[($N^2$-propanamidino)methyl]-6,7-2', 3'-indolomorphinan Dihydrochloride (1; II, R=Et))

Amine 8 (300 mg, 0.677 mmol) and O-methyl propanimidate (molar excess) were dissolved in abs. EtOH and stirred at 50° C. until TLC showed no starting material (24 hr). The crude reaction mixture was concentrated by rotary evaporation and added to brine at pH 10–11, and extracted with EtOAc. The organic phases were combined, dried over $Na_2SO_4$, and the product precipitated as the HCl salt, which was recrystallized from ethanol-ether, to yield 143 of 1, 0.29 mmol, 74%. TLC Rf (A) 0.34. MS(ion spray) (M+1) 499. CHN: $C_{30}H_{36}N_4O_3Cl_2.2H_2O.NaCl$. $^1$H NMR: 11.335 (s, 1H, exch); 10.056 (s, 1H, exch); 9.353 (s, 1H, exch); 9.166 (bs, 1H, exch); 8.910 (s, 1H, exch); 7.374 (s, 1H); 7.314, 7.285 (d, 1H, J=8.3); 7.098, 7.070 (d, 1H, J=8.3); 6.593, 6.566 (d, 1H, J=8.1); 6.485, 6.456 (d, 1H, J=8.1); 5.538 (s, 1H); 4.462, 4.453 (d, 2H, J=2.6); 3.605 (m, 1H); 3.345 (s, 1H); 3.206 (s, 1H); 3.141 (s, 1H); 2.951, 2.934 (d, 1H, J=5.1); 2.84 (m, 1H); 2.804 (bs, 2H); 2.751 (s, 1H) 2.626 (m, 1H); 2.446, 2,422, 2.398, 2.374 (m, 2H, J=7.2); 2.353, 2.329 (m, 1H); 1.870 (s, 1H); 1.638, 1.602 (d, 1H, J=10.8); 1.143, 1.118, 1.093 (t, 3H, J=7.5); 0.957 (m, 1H); 0.550 (m, 2H); 0.253 (m, 2H).

EXAMPLE 6

17-(Cyclopropylmethyl)-6,7-dehydro-4,5α-epoxy-3, 14-dihydroxy-5'-[($N^2$-3-methylpentanamidino) methyl]-6,7-2',3'-indolomorphinan Dihydrochloride (2, II, R=2-Methyl-butyl)

Amine 8 dihydrochloride (200 mg, 0.39 mmol) and a molar excess of O-methyl 3-methylpentanimidate were dissolved in abs. EtOH with TEA and stirred at 50° C. until TLC showed no starting material (24 hr). The residue from the crude reaction mixture was filtered and washed with small portions of cold ethanol, dissolved in MeOH, dried over $Na_2$—$SO_4$. Product was precipitated as the HCl salt, and recrystallized from ethanol-ether to yield 69 mg of 2 (0.112 mmol, 29%); TLC (A) Rf 0.48. MS(ion spray) (M+1) 541. CHN: $C_{33}H_{42}N_4O_3Cl_2.1.5H_2O.2NaCl$. $^1$H NMR: 11.384 (s, 1H, exch); 9.954 (s, 1H, exch); 9.243 (bs, 2H, exch); 9.012 (s, 1H, exch); 8.861 (s, 1H, exch); 7.334 (s, 1H); 7.305, 7.281 (d, 1H, J=7.2); 7.098, 7.074 (d, 1H, J=7.2); 6.619, 6.594 (d, 1H, J=7.5); 6.534, 6.509 (d, 1H, J=7.5); 6.477 (s, 1H, exch); 5.632 (s, 1H, 5Cβ); 4.474, 4.458 (d, 2H, J=4.8); 4.141, 4.112 (d, 1H, J=8.7); 3.25 (m, 2H); 2.922 (m, 2H); 2.780, 2.768 (d, 1H, J=3.6); 2.605 (dd or q, 1H); 2.20–2.138 (m, 2H); 1.825, 1.805–1.744 (m, 2H) 1.322–1.196 (m, 1H); 1.147, 1.122, 1.106, 1.082 (dd, 2H, J=7.3); 0.834 (m, 1H); 0.822, 0.793, 0.764 (t, 3H, J=8.7); 0.785, 0.765 (d, 3H, J=6.0); 0.586 (m, 2H); 0.387 (m, 2H).

EXAMPLE 7

17-(Cyclopropylmethyl)-6,7-dehydro-4,5α-epoxy-3, 14-dihydroxy-5'-[($N^2$-butyramidino)methy]-6,7-2',3'-indolomorphinan Dihydrochloride (5, II, R=Pr).

Amine 8 (200 mg, 0.45 mmol) and a molar excess of O-methyl butyrimidate were heated in 20 mL abs. ethanol at 50° C. for 24 hr with stirring. The solvent was concentrated, and the reaction mixture was poured into ethyl acetate to precipitate the product. The product was filtered and washed with ether, then redissolved in ethanol and dried on sodium sulfate. The product was then converted to the hydrochloride salt, and precipitated from ether. The precipitate was recrystallized from ethanol-ether and dried under high vacuum to yield product 5 (156 mg, 0.27 mmol, 66%). TLC (A) Rf 0.18 (free base), 0.50 (salt). MS(ion spray) (M+1) 513. CHN: $C_{31}H_{38}N_4O_3Cl_2.H_2O.NaCl$. $^1$H NMR: 11.400 (s, 1H, exch); 9.929 (bs, 1H, exch); 9.293 (s, 2H, exch); 9.242 (bs, 1H, exch); 8.987 (bs, 1H, exch); 8.851 (bs, 1H, exch); 7.393, 7.350 (d, 1H, J=8); 7.377 (s, 1H); 7.141, 7.098 (d, 1H, J=8); 6.679, 6.639 (d, 1H, J=8); 6.600, 6.559 (d, 1H, J=8); 6.482 (s, 1H, exch); 5.697 (s, 1H, $C_5p$); 4.480 (d, 2H); 4.148 (d, 1H); 3.25 (d, 1H); 3.109 (s, 1H); 2.987 (t, 2H); 3.0–2.82 (m, 2H); 2.675 (m, 2H) 2.433 (m, 2H); 2.396–2.307 (m, 1H); 1.828, 1.777 (d, 1H, J=10); 1.680, 1.644, 1.606, 1.569 (quint, 2H, J=7); 1.099 (m, 1H); 0.896, 0.859, 0.822 (t, 3H, J=7); 0.680 (m, 2H); 0.484 (m, 2H).

EXAMPLE 8

17-(Cyclopropylmethyl)-6,7-dehydro-4,5α-epoxy-3, 14-dihydroxy-5-[($N^2$-pentanamidino)methyl]-6,7-2', 3'-indolomorphinan Dihydrochloride (6, II. R=Bu)

Amine 8 (200 mg, 0.45 mmol) and a molar excess of O-methylvalerimidate were heated in 20 mL abs. ethanol at 50° C. for 24 hr with stirring. The solvent was concentrated, and the reaction mixture was poured into ethyl acetate to precipitate the product, which was filtered and washed with ether.

The residue was redissolved in ethanol, dried on sodium sulfate and converted to the hydrochloride salt. The salt was precipitated from ether, recrystallized from ethanol-ether and dried under high vacuum to yield δ (88 mg, 0.15 mmol, 33%). TLC (A) Rf 0.11 (free base), 0.50 (salt). MS(ion spray) (M+1) 527. CHN: $C_{32}H_{40}N_4O_3Cl_2.1.5H_2O.NaCl$. $^1$H NMR: 11.440 (s, 1H, exch); 10.026 (bs, 1H, exch); 9.315

(bs, 2H, exch); 9.1 (bs, 1H, exch); 8.897 (s, 1H, exch); 7.394 (s, 1H); 7.377, 7.349 (d, 1H, J=8); 7.138, 7.109 (d, 1H, J=8); 6.675, 6.646 (d, 1H, J=8); 6.585, 6.557 (d, 1H, J=8); 5.683 (s, 1H, C5β); 4.505 (bs, 2H); 4.168 (bs, 1H); 3.669 (s, 1H); 3.30 (m, 1H); 3.084 (m, 1H); 3.010, 2.966 (m, 2H); 2.649 (m, 1H); 2.53 (m, 1H); 2.458, 2.434, 2.405 (t, 2H); 2.081 (s, 1H) 1.796, 1.759 (d, 1H, J=11); 1.61–1.55 (quint, 2H); 1.30–1.22 (m, 2H); 1.12 (m, 1H); 0.883, 0.857, 0.833 (t, 3H, J=7.5); 0.70 (m, 1H); 0.63 (m, 1H); 0.48 (m, 1H); 0.43 (m, 1H).

EXAMPLE 9

17-(Cyclopropylmethyl)-6,7-dehydro-4,5α-epoxy-3, 14-dihydroxy-5'-[N-(β-diethylamino) ethylcarboxyamido]-6,7-2',3'-indolomorphinan Dihydrochloride (38)

Compound 15 (200 mg, 0.377 mmol) in 25 mL dry dichloromethane was brought into solution dropwise with triethylamine. BOP reagent (170 mg, 0.385 mmol) and N,N-diethylethylenediamine (90 mg, 0.75 mmol, 0.1 mL) were added, and the solution was stirred at 25° C. for 24 hr. The reaction mixture was added to ethyl acetate (150 mL), washed 3× with brine at pH 10, and the organic phase dried on sodium sulfate and magnesium sulfate, filtered, and concentrated. The residue was converted to the HCl salt using methanolic HCl and precipitated from ethyl acetate. The product was recrystallized from ethanol-ether, and dried under high vacuum, to yield 217 mg of 38 (0.345 mmol, 91%). TLC (A) Rf 0.49; MS(ion spray) (M+1) 557. CHN: $C_{33}H_{42}N_4O_4Cl_2.3.5H_2O$. $^1H$ NMR: 10.6 (s, 1H, exch); 9.343 (bs, 1H, exch); 9.032 (bs, 1H, exch); 8.889 (t, 1H, exch); 8.62 (bs, 1H, exch); 8.106 (s, 1H); 7.778, 7.734 (d, 1H, J=8); 7.413, 7.370 (d, 1H, J=8); 6.699, 6.658 (d, 1H, J=8); 6.613, 6.572 (d, 1H, J=8); 6.57 (s, 1H, exch); 5.705 (s, 1H, C5β); 4.152 (d, 1H); 3.644 (m, 2H); 3.527, 3.484 (d, 1H, J=8); 3.190–3.133 (m, 8H as 4(—NCH$_2$—)]; 3.024 (s, 1H); 2.679 (m, 2H); 2.586 (s, 1H); 2.43 (d, 2H) 1.831, 1.784 (d, 1H, J=9); 1.262, 1.227, 1.191 (t, 6H); 1.16 (m, 1H); 0.683 (m, 2H); 0.485 (m, 2H).

EXAMPLE 10

17-(Cyclopropylmethyl)-6,7-dehydro-4,5α-epoxy-3, 14-dihydroxy-5'-[N²-(N,N-dimethylglycinamidino) methyl]-6,7-2',3'-indolomorphinan Trihydrochloride (42, II, R=CH$_2$NMe$_2$)

Amine 8 (160 mg, 0.36 mmol) and O-methyl (N,N-dimethyl)-glycinimidate (free base, molar excess), were dissolved in abs. ethanol and maintained with stirring at 50° C. for 72 hr. The solution was concentrated, then poured into ethyl acetate to precipitate the product. The product was recrystallized from ethanol-ether, and converted to the hydrochloride salt to yield 42 (83 mg, 0.13 mmol, 36%). TLC (A) Rf=0.10, (C) Rf=0.30. MS (FAB) 528 (M+1). CHN: $C_{31}H_{40}N_5O_3Cl_3.0.3NaCl.C_2H_6O$. $^1H$ NMR: 11.404 (s, 1H, exch); 10.35 (br, 1H, exch); 9.556 (br, 2H, exch); 9.268 (s, 1H, exch); 8.963 (br, 1H, exch); 7.423 (s, 1H); 7.338, 7.309 (d, 1H, J=8.7); 7.163, 7.135 (d, 1H, J=8.4); 6.643, 6.619 (d, 1H, J=7.2); 6.554, 6.525 (d, 1H, J=8.7); 6.505 (s, 1H, exch); 5.652 (s, 1H, C$_5$H); 4.567 (s, 2H); 4.161, 4.141 (d, 1H, J=6); 3.471 (m, 1H); 3.402 (s, 1H); 3.353 (m, 1H); 3.297, 3.272 (d, 1H, J=6.3); 3.122, 3.102 (d, 1H, J=6); 3.037 (s, 1H); 2.984 (s, 1H); 2.667 (m, 2H); 2.582 (m, 1H); 2.533 (s, 1H); 2.504 (s, 6H, N(CH$_3$)$_2$); 1.812, 1.775 (d, 1H, J=11); 1.142 (m, 1H); 0.715 (m, 1H) 0.634 (m, 1H); 0.524 (m, 1H); 0.439 (m, 1H).

EXAMPLE 11

17-(Cyclopropylmethyl)-6,7-dehydro-4,5α-epoxy-3, 14-dihydroxy-51'-[(4-dimethylaminobutyryl) aminomethyl]-6,7-2',3'-indolomorphinan Dihydrochloride (43)

Compound 8 (as the free base, 179 mg, 0.404 mmol) was combined with 4-dimethylaminobutyric acid (75 mg, 0.444 mmol) and BOP reagent (200 mg, 0.452 mmol) in dry CH$_2$Cl$_2$ and stirred at 25° C. 24 hr. The crude mixture was poured into 150 mL ethyl acetate and washed 3× with alkaline brine. The organic portion was dried on Na$_2$SO$_4$, and precipitated as the HCl salt with methanolic HCl, to yield 82 mg of 43 (0.130 mmol, 32%). TLC (A) Rf=0.34. MS (FAB) 557 (M+1). CHN: $C_{33}H_{42}N_4O_4Cl_2.2H_2O.0.5NaCl$. $^1H$ NMR: 11.250 (s, 1H, exch); 10.75 (br, 1H, exch); 9.231 (s, 1H, exch); 8.943 (br, 1H, exch); 8.427, 8.410, 8.390 (t, 1H, J=5.1 and 6); 7.269, 7.240 (d, 1H, J=8.7); 7.167 (s, 1H); 7.001, 6.972 (d, 1H, J=8.7); 6.631, 6.603 (d, 1H, J=8.4); 6.550, 6.521 (d, 1H, J=8.7); 6.395 (s, 1H, exch); 5.636 (s, 1H, C$_5$H); 4.255, 4.238 (d, 2H, J=5.1); 4.141, 4.125 (d, 1H, J=4.8); 3.418, 3.410 (d, 1H, J=5.1); 3.353 (s, 1H); 3.247 (s, 1H); 3.202 (m, 1H); 3.105 (s, 1H); 3.048 (s, 1H); 2.971 (s, 1H); 2.942, 2.930 (d, 1H, J=8.7); 2.650 (s, 6H); 2.585 (s, 1H); 2.195, 2.171, 2.146 (t, 2H, J=7.2 and 7.5); 1.854 (m, 2H); 1.768, 1.732 (d, 1H, J=11); 1.085 (m, 1H); 0.680 (m, 1H); 0.607 (m, 1H); 0.448 (m, 1H); 0.416 (m, 1H).

EXAMPLE 12

17-(Cyclopropylmethyl)-6,7-dehydro-4,5α-epoxy-3, 14-dihydroxy-5 '-[N²-(4-dimethylaminobutyrylamidino)methyl]-6,7-2',3'-indolomorphinan Trihydrochloride (44, II, R=CH$_2$CH$_2$CH$_2$—NMe$_2$)

Amine 8 (free base, 220 mg, 0.497 mmol) and O-methyl 4-(dimethylamino)butyrimidate (free base, molar excess) were dissolved in abs. ethanol and maintained with stirring at 50° C. for 72 hr. The solution was concentrated, then added to ethyl acetate to precipitate the product. The product was recrystallized from ethanol-ether and converted to the hydrochloride salt, to yield product 44 (95 mg, 0.143 mmol, 29%). TLC (A) Rf=0.0, (C) Rf=0.09. MS (FAB) 556 (M+1). CHN: $C_{31}H_{44}N_5O_3Cl_3.1.5H_2O.0.5NaCl0.5C_2H_5OH$. $^1H$ NMR: (taken as the free base) 11.252 (s, 1H); 7.303 (s, 1H); 7.295, 7.268 (d, 1H, J=8.1); 7.056, 7.029 (d, 1H, J=8.1); 6.561, 6.534 (d, 1H, J=8.1); 6.461, 6.434 (d, 1H, J=8.1); 5.480 (s, 1H, C$_5$H); 4.745 (s, 1H); 4.345 (s, 2H); 3.269, 3.250 (d, 2H, J=5.7); 3.089 (s, 1H); 3.025 (s, 1H); 2.728 (m, 1H); 2.694 (m, 1H); 2.681 (s, 1H); 2.489, 2.467 (d, 2H, J=6.6); 2.408, 2.386 (d, 2H, J=6.6); 2.293 (m, 3H); 2.157 (m, 3H); 2.052 (s, 6H); 1.601, 1.564 (d, 1H, J=11); 0.883 (m, 2H); 0.488 (m, 2H); 0.159, 0.144 (d, 2H, J=4.5).

EXAMPLE 13

17-(Cyclopropylmethyl)-6,7-dehydro-4,5α-epoxy-3, 14-dihydroxy-5'-[N-(β-dimethylamino) ethylcarboxamido]-6,7-2',3'-indolomorphinan Dihydrochloride (45)

Compound 15 (200 mg, 0.377 mmol) in 25 mL dry dichloromethane was brought into solution by dropwise addition of triethylamine. BOP reagent (170 mg, 0.385 mmol) and N,N-dimethylethylenediamine (66 mg, 0.75 mmol, 0.08 mL) were added, and the solution was stirred at 25° C. for 5 hr. The reaction mixture was added to ethyl acetate (150 mL) and washed 3x with brine at pH 10. The organic phase was dried over sodium sulfate and magnesium sulfate, filtered, and concentrated. The free base was precipitated from hexane to remove TEA and N,N-dimethylethylenediamine, then converted to the HCl salt and precipitated from ethyl acetate. The precipitate was recrystallized from ethanol-ether and dried at high vacuum to yield 123 mg of 45, 0.204 mmol, 54%. TLC (A) Rf=0.28; MS(ion spray) (M+1) 529. CHN: $C_{31}H_{38}N_4O_4Cl_2 \cdot H_2O$. $^1H$ NMR: 11.678 (s, 1H, exch); 10.657 (s, 1H, exch); 9.343 (bs, 1H, exch); 9.030 (bs, 1H, exch); 8.803, 8.787, 8.769 (t, 1H, exch, amide NH); 8.095 (s, 1H); 7.773, 7.746 (d, 1H, J=8); 7.413, 7.370 (d, 1H, J=8); 6.685, 6.657 (d, 1H, J=8); 6.603, 6.577 (d, 1H, J=8); buried, 6.58 (s, 1H, exch, $C_{14}$—OH); 5.700 (s, 1H, $C_5\beta$); 4.163 (bs, 1H); 3.669, 3.649, 3.632, 3.612 (qt, 2H); 3.259, 3.240, 3.220 (t, 2H); 3.28 (m, 1H); 3.089 (m, 2H); 3.034 (s, 1H); 2.988 (m, 1H); 2.88–2.86 (m, 1H); 2.658 (m, 1H); 2.572 (s, 1H); 1.817, 1.784 (d, 1H, J=10); 1.141 (m, 1H); 0.692 (m, 1H); 0.647 (m, 1H); 0.487 (m, 1H); 0.452 (m, 1H).

EXAMPLE 14

Evaluation of Antagonist and Agonist Activity

A. Smooth Muscle Assays

1. Guinea Pig Ileal Longitudinal Muscle (GPI). Ilea from guinea pigs were taken approximately 10 cm from the ileocecal junction, and a strip of longitudinal muscle with the myenteric plexus attached was prepared by the method of H. B. Rang et al., *Brit. J. Pharmacol.*, 22, 356 (1964). A 1 cm portion of this strip was then mounted between two platinum electrodes placed in a 10 ml organ bath and connected to an isometric transducer; contractions were recorded on a polygraph. Contractions of the ileal strip were initiated by supramaximal rectangular pulses in all preparations (80 V of 0.5 ms duration at a frequency of 0.1 Hz). Krebs bicarbonate solution containing 1.25 µM chlorpheniramine maleate was the bathing solution and was continuously bubbled with 95% $O_2$ and 5% $CO_2$. The organ bath was maintained at 36°–37° C. The longitudinal muscle strip was allowed to equilibrate with continuous stimulation for a minimum of 90 min. Cumulative concentration-response curves were determined after drugs were added to the bath in preselected amounts and washed out with buffer after noting their maximum effects.

2. Mouse Vas Deferens (MVD). This assay was performed according to the description by G. Henderson et al., *Brit. J. Pharmacol.*, 46, 764 (1972). Both vasa deferentia were dissected out of mice and mounted singly through two platinum ring electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in preselected amounts and washed out after noting their maximum effects.

B. Pharmacology

Each compound (100 nM) was incubated for 15 min with the mouse vas deferens (MVD) and guinea pig ileum (GPI) preparations prior to adding graded doses of a standard agonist for determination of an $IC_{50}$ value. The standard agonists employed were [D-Ala$^2$, D-Leu$^5$]enkephalin (DADLE) (D), morphine (M), and ethylketazocine (EK); these are selective for delta (D), mu (M) and kappa (EK) opioid receptors. Concentration-response curves were obtained in the absence (control) and the presence of the antagonist are expressed as $IC_{50}$ values. The $IC_{50}$ ratio represents the $IC_{50}$ in the presence of the antagonist divided by the control $IC_{50}$ value in the same tissue. Therefore, a high $IC_{50}$ ratio represents a correspondingly high degree of antagonism at a particular receptor. This $IC_{50}$ ratio was employed to calculate the Ke value using the equation Ke=[antagonist]/($IC_{50}$ ratio-1). Therefore, a low Ke represents a correspondingly high degree of binding at a particular receptor. The results of these bioassays are summarized on Table II, below.

TABLE II

| | EK$^a$ (GPI) | | M$^a$ (GPI) | | D$^a$ $^D$(MVD) | | Selectivity | |
|---|---|---|---|---|---|---|---|---|
| Compound number & structure (R=)$^b$ | Ke$^e$ | $IC_{50}$$^c$ ratio$^d$ | Ke | $IC_{50}$ ratio | Ke | $IC_{50}$ ratio | κ/µ | κ/δ |
| alkyd-amidines: | | | | | | | | |
| 3 | 0.81 nM | 124 ± 33 | 8.04 nM | 13.4 ± 2.2 | f | 2.81 ± 0.62 | 9 | 44 |
| 1 | 0.66 nM | 159 ± 43 | 9.71 nM | 11.3 ± 2.6 | f | 2.28 ± 0.57 | 14 | 69 |

TABLE II-continued

| Compound number & structure (R=)[b] | EK[a] (GPI) Ke[e] | IC$_{50}$[c] ratio[d] | M[a] (GPI) Ke | IC$_{50}$ ratio | D[a] D(MVD) Ke | IC$_{50}$ ratio | Selectivity κ/μ | κ/δ |
|---|---|---|---|---|---|---|---|---|
| 5 | 0.54 nM | 185 ± 49 | 5.84 nM | 18.2 ± 3.9 | f | 3.00 ± 0.51 | 10 | 62 |
| 6 | 0.23 nM | 439 ± 100 | 6.80 nM | 15.7 ± 4.0 | 26.9 nM | 4.71 ± 1.06 | 28 | 93 |
| 2 | 0.25 nM | 394 ± 97 | 3.27 nM | 31.6 ± 10.7 | f | 1.19 ± 0.51 | 12 | 310 |
| Amide-amines: | | | | | | | | |
| 45 | 0.568 nM | 177 ± 54 | 3.41 nM | 30.3 ± 3.6 | f | 1.51 ± 0.42 | 6 | 117 |
| 38 | (10 nm) 0.320 nM | 31.8 ± 7.7 | (50 nm) 3.14 nM | 17.1 ± 2.1 | (100 nM) f | 1.95 ± 0.56 | 16 | 329 |
| 43 | 0.505 nM | 199 ± 62 | 5.56 nM | 19.0 ± 6.2 | f | 1.20 ± 0.72 | 10 | 166 |
| amidine-amines: | | | | | | | | |
| 42 | 0.183 nM | 547 ± 125 | 11.1 nM | 10.0 ± 0.4 | 25.6 nM | 4.91 ± 1.38 | 55 | 111 |
| 44 | 0.147 nM | 679 ± 273 | 9.01 nM | 12.1 ± 3.4 | f | 2.71 ± 0.44 | 61 | 250 |
| norBinaltorphimine | 0.56 nM | (179) | 14 nM | (8.14) | 14 nM | (8.14) | 22 | 22 |

[a]Agonists: kappa (EK) (ethylketazocine) mu (M) (morphine) delta (D) (DADLE)
[b]All antagonist concentrations were 100 nM except where noted.
[c]IC$_{50}$ = conc. of drug producing 50% inhibition of maximum response.
[d]IC$_{50}$ ratio = IC$_{50}$ agonist + antagonist/IC$_{50}$ agonist
[e]Ke = [antagonist]/IC$_{50}$ ratio-1.
[f]The Ke value cannot be determined because the IC$_{50}$ ratio is not significantly different from 1.

The compounds tested showed little or no agonistic activity in either the GPI or MVD preparation. However, the compounds showed significant antagonistic potency toward the kappa opioid receptor agonist, ethylketazocine (EK), in the GPI. This was manifested by displacement of the EK concentration-response curve to higher concentration by factors up to 680 (IC$_{50}$ ratio) in the presence of 100 nM of the test compounds. These results contrast with the observation that these compounds are considerably less effective in antagonizing the effect of morphine (a mu receptor-selective agonist). In this connection, it can be seen that the morphine IC$_{50}$ ratios at the same concentration of antagonist (100 nM) are not greater than one-sixth of those $IC_{50}$ ratios obtained with EK. Likewise, the EK results contrast with the observation that these compounds have considerably less ability to antagonize the activity of DADLE (delta-receptor agonist) at the same antagonist concentration (100 nM). This is demonstrated by $IC_{50}$ ratios not greater than one-thirtieth of those ratios obtained with EK. Thus, the compounds are highly selective kappa-opioid receptor antagonists. Compounds 2, 5, 6, 38, 42, 43, and 44 are all more potent than the most potent known kappa antagonist, norBNI (norBinaltorphimine), and of these, 6, 42, and 44, are also more selective. Of these ompounds, it appears that 44 possesses the greatest potency and selectivity.

Compound δ was tested in vivo using the mouse writhing procedure of G. Hayashi et al., *Eur. J. Pharmacol.*, 85, 163 (1982). It is believed that this response is mediated by kappa receptors. Mice were treated with 50 nmol of the agonist (morphine, DADLE, or the kappa selective agonist U50488H) and the 6 was administered subcutaneously (sc) at 4 mg/kg. The $ED_{50}$ ratios [(agonist +6)/−agonist control] for morphine, DADLE, and U50488H, respectively were 1.63, 0.25, and 3.77. Therefore, the observed inhibition exhibited by 6 of the writhing inhibition of morphine, DADLE, or U50488H in the whole animal model correlates with that observed in vitro, and demonstrates that 6 is indeed a selective kappa antagonist.

C. Discussion

The 5'-substituted naltrindole compounds listed on Table II display a unique pharmacological profile in that they exhibit substantially greater antagonist potency at kappa-opioid receptors than at mu or delta opioid receptors. Moreover, compounds 6, 42, and 44 are more potent and selective than the selective kappa antagonist, norBNI. The in vivo antagonist selectivity parallels that observed in the GPI preparation. Because these compounds exhibit no agonist effect in GPI or MVD, these can be regarded as "Pure" kappa opioid receptor antagonists. Therefore, compounds 6, 42, 44, and the other compounds of the present invention which exhibit kappa opioid receptor antagonist activity should be useful for pharmacological studies of opioid receptor activity and function and may be therapeutically useful in conditions where selective blockage of kappa receptors is desired. This includes blockage of the appetite response, blockage of paralysis due to spin al trauma, and a variety of other physiologic activities that may be mediated through kappa receptors.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of the formula:

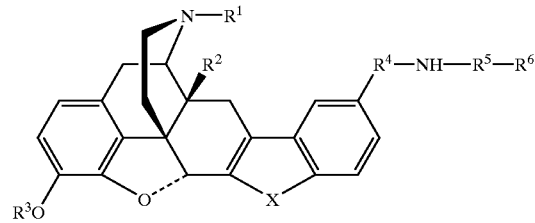

wherein $R^1$ is ($C_1$–$C_5$)alkyl, $C_3$–$C_6$(cycloalkyl)alkyl, $C_5$–$C_7$(cycloalkenyl)alkyl, ($C_6$–$C_{12}$)aryl ($C_7$–$C_{12}$)aralkyl, trans ($C_4$–$C_5$)alkenyl, allyl or furan-2-ylalkyl, $R^2$ is H, OH or $O_2C(C_1$–$C_5)$alkyl; $R^3$ is H, ($C_7$–$C_{10}$)aralyl, ($C_1$–$C_5$)-alkyl or ($C_1$–$C_5$)alkylCO; X is O, S or NY, wherein Y is H or ($C_1$–$C_5$)alkyl; $R^4$ is $CH_2$ or C=O, $R^5$ is $CH_2$, C=O or C=NH and $R^6$ is ($C_1$–$C_4$)alkyl or NH($C_1$–$C_4$)alkyl, optionally substituted by a non-terminal ($C_1$–$C_2$)alkyl group or by $N(R^7)(R^8)$ wherein $R^7$ and $R^8$ are individually H or ($C_1$–$C_3$) alkyl, with the proviso that one of $R^4$ or $R^5$ is $CH_2$, and the pharmaceutically acceptable salts thereof.

2. A compound of claim 1 wherein $R^1$ is $C_3$–$C_6$(cycloalkyl)$C_1$–$C_5$(alkyl).

3. A compound of claim 2 wherein $R^1$ is $C_3$–$C_6$(cycloalkyl)-methyl.

4. A compound of claim 3 wherein $R^1$ is cyclopropyl-methyl.

5. A compound of claim 1 wherein $R^2$ is H, OH or OAc.

6. A compound of claim 5 wherein $R^3$ is H.

7. A compound of claim 1 wherein X is O, NH or $NCH_3$.

8. A compound of claim 1 wherein $R^4$ is $CH_2$ and $R^5$ is C=NH.

9. A compound of claim 1 wherein $R^6$ is ($C_1$–$C_4$)alkyl, optionally substituted by a nonterminal $CH_3$ group, $N(CH_3)_2$ or $N(CH_2CH_3)_2$.

10. A method for selectively blocking the binding of a kappa opioid-receptor agonist to kappa opioid receptors in mammalian tissue comprising said receptors, said method comprising contacting said tissue with an effective amount of a compound of claim 1 to block said receptors.

* * * * *

UNITED STATES PATENT AND TRADEMARK OFFICE
CERTIFICATE OF CORRECTION

PATENT NO. : 6,534,514 B1 Page 1 of 1
DATED : March 18, 2003
INVENTOR(S) : Philip S. Portoghese, Sandra L. Olmsted It is certified that error appears in the above-identified patent and that said Letters Patent is hereby corrected as shown below:

<u>Title page,</u>
Item [57], ABSTRACT, delete "(C6-C12)aralkyl" and insert -- (C7-C12)aralkyl --
Therefor; also delete "(C6-C10)aralkyl" and insert -- (C7-C10)aralkyl --
therefor.

<u>Column 18,</u>
Line 21, delete "(C7-C10)aralyl" and insert -- (C7-C10)aralkyl -- therefor.

Signed and Sealed this

Eighteenth Day of May, 2004

JON W. DUDAS
*Acting Director of the United States Patent and Trademark Office*